United States Patent

Jacobsen et al.

[11] Patent Number: 5,647,575
[45] Date of Patent: Jul. 15, 1997

[54] VOLUMETRIC SHAFT/VALVE

[75] Inventors: Stephen C. Jacobsen; Clark C. Davis, both of Salt Lake City, Utah

[73] Assignee: Sarcos Group, Salt Lake City, Utah

[21] Appl. No.: 470,034

[22] Filed: Jun. 6, 1995

Related U.S. Application Data

[62] Division of Ser. No. 157,693, Nov. 23, 1993.

[51] Int. Cl.$^6$ ........................................ F16K 3/26
[52] U.S. Cl. ........................ 251/325; 137/625.38
[58] Field of Search ........................ 137/576, 592, 137/625.38; 417/547, 545; 251/325

[56] References Cited

U.S. PATENT DOCUMENTS

| | | | |
|---|---|---|---|
| 247,401 | 9/1881 | Pease | 417/547 |
| 412,416 | 10/1889 | Rodgers | 251/325 |
| 556,153 | 3/1896 | Lines | 417/547 |
| 749,248 | 1/1904 | Willmann | 417/549 |
| 1,489,540 | 4/1924 | Miller | 417/547 |
| 1,587,172 | 6/1926 | Muller | 251/325 |
| 1,726,402 | 8/1929 | Lurcott | 417/547 |
| 3,164,170 | 1/1965 | Gutter | 137/625.38 |
| 3,527,386 | 9/1970 | Close et al. | 417/547 |
| 4,209,040 | 6/1980 | Peters | 251/325 |

FOREIGN PATENT DOCUMENTS 1613676  12/1990  U.S.S.R. ................ 417/549

Primary Examiner—Timothy Thorpe
Assistant Examiner—Peter G. Kurytnyk
Attorney, Agent, or Firm—Thorpe, North & Western, L.L.P.

[57] ABSTRACT

A valve which may be used with a pump which includes a housing having an interior cavity therein with an inlet and an outlet leading through the housing into the cavity. A resilient sheet of material with an aperture formed therein is disposed in the cavity dividing it into first and second compartments with the inlet leading into the first compartment and the outlet leading from the second compartment. An elongated shaft adapted for reciprocating movement is disposed within and aligned with the cavity and extends through the aperture in the sheet of resilient material. An interior passage extends lengthwise in the shaft and includes first and second openings in the passage which may be positioned so that the first opening is located in the first compartment and the second opening is located in the second compartment, providing a fluid communication between the two compartments.

3 Claims, 2 Drawing Sheets

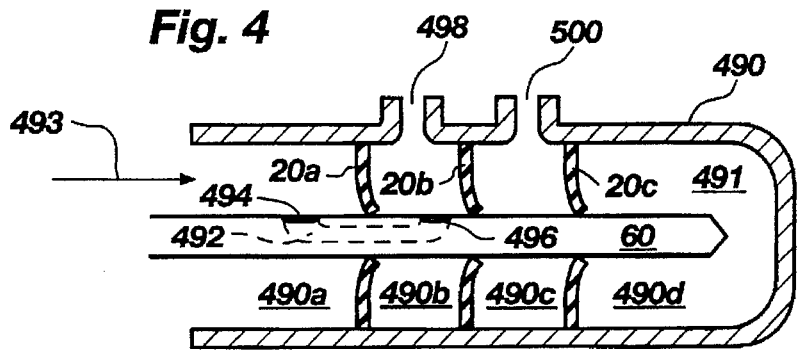
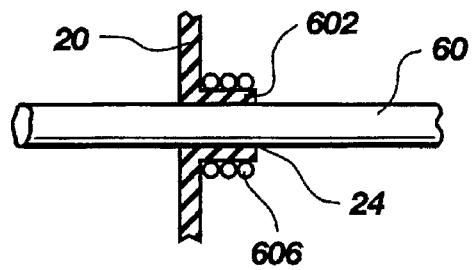
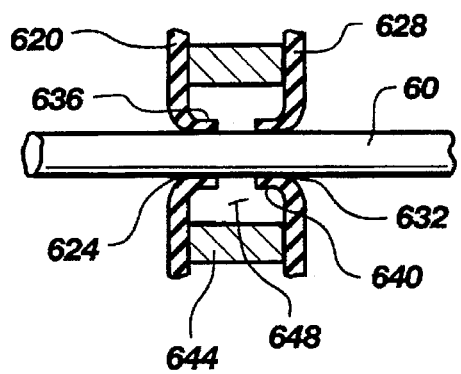
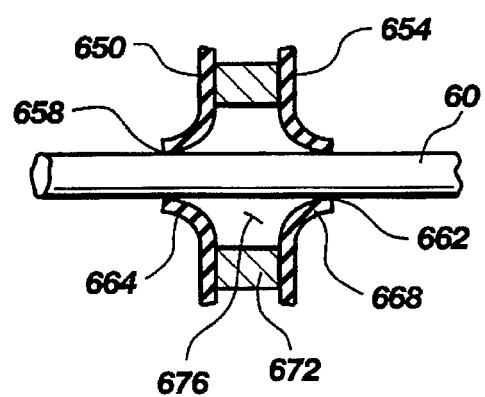

VOLUMETRIC SHAFT/VALVE

This application is a divisional of application Ser. No. 08/157,693, filed Nov. 23, 1993 now allowed.

BACKGROUND OF THE INVENTION

This invention relates to a lightweight, inexpensive volumetric pump, suitable for a variety of uses including medical systems such as intravenous (IV) therapy systems and the like. More particularly, the present invention concerns a valve for use in conjunction with a pump which regulates and controls rates and volumes of fluid flow.

The intravenous administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently requires the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

SUMMARY OF THE INVENTION

It is an object of the invention to provide a new and improved valve for a volumetric pump which is especially suitable for use in IV administration sets, other medical systems, and the like.

It is a further object of the invention to provide such a valve which is easy to manufacture and utilizes low cost parts.

It is another object of the invention to provide such a valve design in which tight tolerances are not required.

It is also an object of the invention to provide such a valve which is efficient and reliable.

It is an additional object of the invention to provide such a valve which may be readily miniaturized.

It is still another object of the invention, in accordance with one aspect thereof, to provide such a valve whose flow rate may be readily changed.

The above and other objects of the invention are realized in a specific illustrative embodiment of a valve which utilizes a simple circumferential polymeric seal, or sphincter seal to retain and prevent loss or leaking of the fluid.

One illustrative embodiment of the invention includes a housing having a cavity therein. A fluid inlet and a fluid outlet are disposed through the housing and into the cavity. A sheet of resilient material is disposed in the cavity dividing the cavity into first and second compartments with the fluid inlet positioned to allow the flow of fluid into the first compartment and the fluid outlet positioned to allow the flow of fluid out of the second compartment. The sheet of resilient material has an aperture formed therein and an elongate shaft is disposed within and aligned with the cavity and extends through the aperture in the sheet. The shaft is adapted for reciprocating movement within the cavity and the elongate interior passage extends length wise through the shaft to first and second openings in opposite ends of the passage. The openings are spaced sufficient far from one another in the shaft so that when the shaft is positioned through the aperture in the resilient material, one opening may be located in the first compartment and the other opening may be located in the second compartment to allow fluid to communicate between the two compartments. The elongated shaft being adapted for reciprocating movements may be moved back and forth in the aperture so that one or the other of the openings passes through the aperture in the sheet and in so doing shuts off the communication between the first and the second compartments, the aperture in the sheet being plugged by that portion of the elongated shaft which extends beyond the respective opening, thus acting as a valve between the first and second compartments.

A variety of driver mechanisms and control methods may be provided to cause the shaft to reciprocate within the cavity to produce the valving action, including ratchet drives, magnetic linear step motors, rotary-to-linear crank drives, and screw drive mechanisms.

A variety of sphincter seals and similar mechanisms may be provided to control flow in the valve, and a electro mechanical sensors may be provided to detect over- or underpressure of fluid in the valve, or other mechanisms.

BRIEF DESCRIPTION OF THE DRAWINGS

The above and other objects, features and advantages of the invention will become apparent from a consideration of the following detailed description presented in connection with the accompanying drawings in which:

FIG. 4 is a side, cross-sectional view of another embodiment of a valve according to the invention;

FIG. 5 is a fragmented, side, cross-sectional view of a spring assisted seal arrangement suitable for use in the present invention;

FIG. 6 is a fragmented, side, cross-sectional view of a duplex, inwardly turned sphincter seal arrangement suitable for use in the present invention; and FIG. 7 is a fragmented, side, cross-sectional view of a duplex, outwardly turned sphincter seal arrangement suitable for use in the present invention.

DETAILED DESCRIPTION OF THE DRAWINGS

Figure 1:
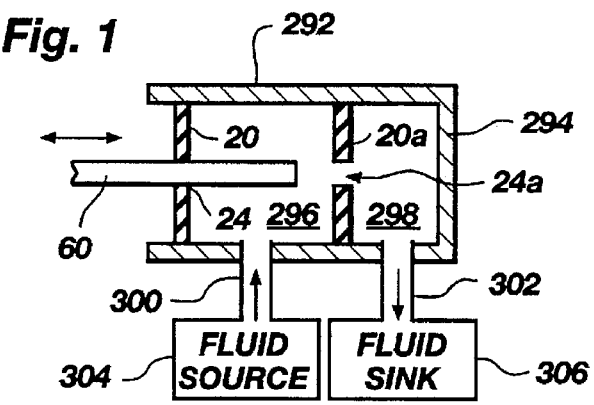
FIG. 1 is a side, cross-sectional view of a valve utilizing sphincter seals, made in accordance with the principles of the present invention.

FIG. 1 shows a side, cross-sectional view of a valve using sphincter seals in accordance with the invention. In this embodiment, an elongate housing 292 is formed of suitable rigid material with a closed end 294. The other end is closed by a resilient sheet of material 20 with an aperture 24 through which a shaft 60 passes, forming a sphincter seal as described below.

The aperture 24 is preferably shaped similarly to the cross-sectional shape of the shaft 60 and is preferably the same or slightly smaller in size, in order to completely surround and grip the shaft 60 to form a sphincter seal and prevent fluid from escaping from within the housing 292. As the aperture 24 is formed in a resilient sheet of material 20, the aperture 24 conforms to the shape of the shaft 60 even if their shapes are not identical, though it would be obvious to those skilled in the art that the more the shapes differ, the less effective the seal will be.

A second sheet of resilient material 20a with an aperture 24a is disposed within the housing 292, dividing it into two cavities 296 and 298, with the aperture 24a serving as a passage therebetween. Unlike previous embodiments of sphincter seals, the shaft 60 passes only selectively, rather than continuously, through the aperture 24a.

A fluid inlet 300 is formed in the housing 292 leading into the cavity 296, and a fluid outlet 302 is formed in the housing leading from the cavity 298. A fluid source 304 is connected to the fluid inlet 300, and a fluid sink 306 is connected to the fluid outlet 302. One or both of the source 304 and sink 306 is pressurized to urge fluid from the source to the sink through the valve.

In operation, when the shaft 60 is withdrawn from the aperture 24a by movement toward the cavity 296, the aperture serves as a passage between the cavities 296 and 298, allowing fluid to flow from the fluid source 304, through the inlet 300, into the cavity 296, through the aperture 24a, into the cavity 298, through the outlet 302, and into the fluid sink 306. When the shaft 60 is placed into the aperture 24a by movement toward the cavity 298, a sphincter seal is formed and communication between the cavities 296 and 298 is blocked, stopping fluid flow. In this manner, the structure of FIG. 7 operates as a valve.

Figure 2:
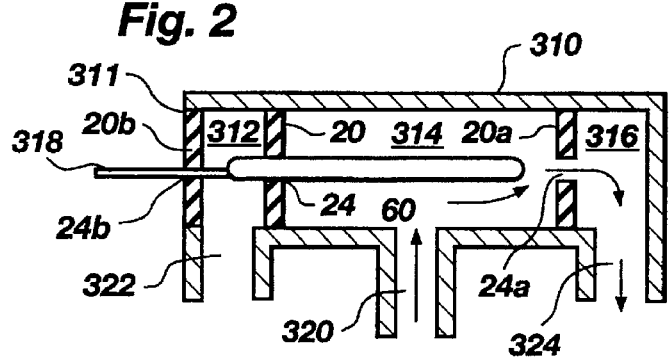
FIG. 2 is a side, cross-sectional view of another embodiment of a valve, also utilizing sphincter seals, made in accordance with the principles of the present invention.

FIG. 2 shows a side, cross-sectional view of another embodiment of a valve using sphincter seals according to the invention, which can be used to switch fluid flow from one destination to another, or stop flow altogether. In this embodiment, a housing 310 is divided into three interior cavities 312, 314, and 316 by two sheets of resilient material 20 and 20a, each having an aperture 24 and 24a, respectively. An elongate shaft 60 moves back and forth through the cavities and apertures, driven by a drive shaft 318 which passes through an aperture 24b in a sheet of resilient material 20b disposed in an opening 311 in the side of the housing 310, forming a sphincter seal as previously described. An inlet conduit 320 leading from a fluid source (not shown) leads into the middle cavity 314. Outlet conduits 322 and 324 lead out of cavities 312 and 316, respectively, to fluid sinks (not shown). Either the fluid source or fluid sinks, or both, are pressurized to urge fluid from the source to the sinks. The shaft 60 selectively passes through the apertures 24 and 24a, selectively forming sphincter seals and blocking fluid flow between the cavities. The shaft 60 may be made long enough to enable it to pass through both apertures 24 and 24a at the same time, completely blocking fluid flow, or may be made shorter so that it is unable to pass through both apertures at the same time.

In operation, when the shaft 60 moves toward the cavity 312, it passes through the aperture 24, forming a sphincter seal therein and blocking fluid flow between the cavities 312 and 314. At the same time, the shaft 60 comes out of the aperture 24a, opening the aperture and enabling fluid to flow from the inlet cavity 314 into the cavity 316 and through the outlet conduit 324 to the fluid sink. When the shaft 60 moves toward the cavity 316, it passes through the aperture 24a, forming a sphincter seal therein and blocking fluid flow between the cavities 314 and 316. At the same time, the shaft comes out of the aperture 24, opening the aperture and enabling fluid to flow from the inlet cavity 314 into the cavity 312 and through the inlet conduit 322 to the fluid sink. If the shaft has been made long enough, it may be centered in the cavity 314, passing through both apertures 24 and 24a and blocking all fluid flow.

Figure 3:
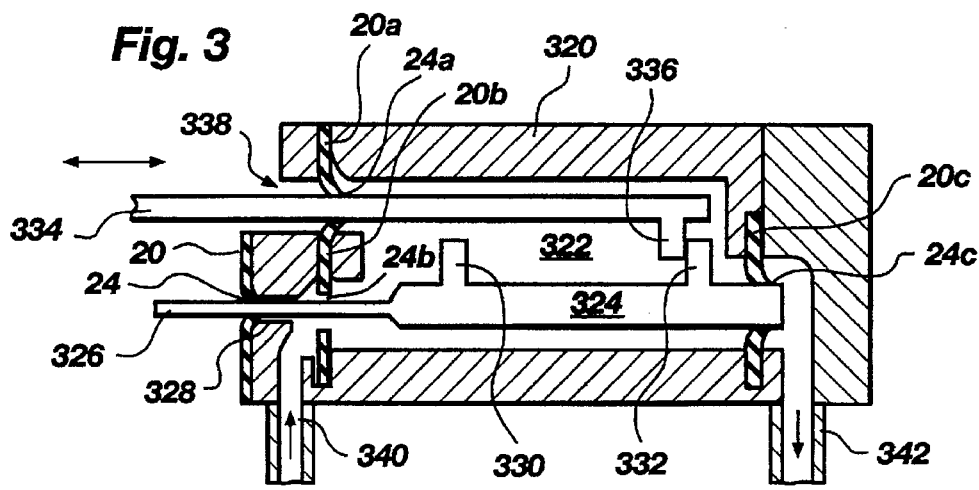
FIG. 3 is a side, cross-sectional view of a spool valve mechanism for use in volumetric pumps of the present invention for controlling the flow of fluid.

FIG. 3 shows a side, cross-sectional view of a spool valve mechanism for controlling the flow of fluid, combined with a pump similar to that of FIG. 3. This embodiment of the invention comprises a housing 320 containing an interior cavity 322. An elongate valve shaft 324 is disposed inside the cavity 322, and an elongate drive shaft 326, of smaller diameter than the valve shaft 324 in the preferred embodiment, is connected to one end of the valve shaft. The drive shaft 326 passes through a passage 328 formed in the housing to extend from the cavity 322 to the exterior. A resilient sheet of material 20 having an aperture 24 is disposed on the housing on the exterior side of the passage 328, and the drive shaft 326 passes through the aperture to form a sphincter seal as previously described. The drive shaft 326 can be used to move the valve shaft 324 back and forth in a reciprocating motion, or merely to stabilize the valve shaft in position, or simply not be used or removed from the apparatus.

The valve shaft 324 includes two flanges 330 and 332 spaced apart from one another. The flanges may extend only partially around the circumference of the valve shaft 324, as shown, or completely around, if desired, though in the latter case, the bottom of the cavity 322 would need to be lowered from what is shown in the drawing.

A piston 334 is disposed in the cavity above the valve shaft 324 and substantially parallel thereto. A tab 336 extends downwardly from the piston sufficiently far to abut either of the flanges 330 or 332 when the piston is moved longitudinally a sufficient distance. The piston 334 extends from the cavity to the exterior of the housing 320 through a passage 338 formed in the housing. A resilient sheet of material 20a, with an aperture 24a, is disposed across the passage 338, and the piston passes through the aperture to form a sphincter seal as previously described.

An inlet conduit 340 passes through the housing into the cavity 322, near the connection of the valve shaft 324 to the drive shaft 326. A resilient sheet of material 20b, with an aperture 24b, is disposed across the inlet conduit substantially parallel to the sheet 20, with the apertures 20 and 20b aligned along the drive shaft 326. The aperture 24b is larger than the aperture 24, enabling the drive shaft 326 to pass through the aperture 24b without forming a sphincter seal, though the aperture 24b is small enough to form a sphincter seal with the valve shaft 324 when the latter passes therethrough.

An outlet conduit 342 passes through the housing into the cavity 322 near the opposite end of the valve shaft 324 from the inlet conduit 340. A resilient sheet of material 20c with an aperture 24c, of approximately the same size as the aperture 24b and aligned therewith, is disposed across the outlet conduit substantially parallel to the sheet 20b. The valve shaft 324 selectively passes through the aperture 24c, forming a sphincter seal therewith when passing through it.

The inlet and outlet conduits are attached to a fluid source and a fluid sink, respectively (not shown).

The valve shaft 324 may be made long enough so that when it is centered between the sheets 20b and 20c it passes through both corresponding apertures 24b and 24c and forms sphincter seals with both. Alternatively, the shaft may be made short enough so that when centered between the two sheets it passes through neither aperture. The valve shaft may be moved back and forth by either the drive shaft 326 attached to suitable drive means, or the piston 334 attached to suitable drive means. If moved by the piston 324, the shaft 324 is moved in the following way: to cut off fluid flow to the outlet conduit 342, the piston is moved toward the outlet conduit until the tab 336 abuts the flange 332 on the valve shaft 324 and pushes the shaft into the aperture 24c. To cut off fluid flow from the inlet conduit 340, the piston is moved toward the inlet conduit 340 until the tab 336 abuts the flange 330 on the valve shaft 324 and pushes the shaft into the aperture 24b. The location of the drive shaft 326 through the aperture 24b does not prevent fluid flow from the inlet conduit into the cavity since, as previously noted, the aperture is of a larger diameter than the drive shaft. The positive and negative pressures required to cause fluid flow from the fluid source into the cavity 322, and from the cavity 327 to the fluid sink are produced by the motion of the piston 334, i.e., a pumping action.

FIG. 4 shows another embodiment of a valve according to the invention, comprising a generally elongate housing 490 defining an elongate internal cavity 491 with three sheets of resilient material 20a, 20b, and 20c disposed therein, each sheet containing an aperture for formation of sphincter seals, as previously described. The sheets 20a, 20b, and 20c are spaced from each other, forming four fluid compartments 490a, 490b, 490c, and 490d in the cavity 491. A shaft 60 is disposed in the cavity 491 through the aligned apertures in the sheets, forming sphincter seals therewith. The shaft 60 contains an internal passage 492 running partially along its length with spaced openings 494 and 496 at each end of the passage 492, in fluid communication with the cavity 491.

An inlet 498 is formed through the housing wall into the compartment 490b, and an outlet 500 is formed through the housing wall into the adjacent compartment 490c. The openings 494 and 496 are spaced such that when the opening 494 is located in the compartment 490b, the opening 496 is located in the compartment 490c, providing fluid communication from the inlet 498, through the compartment 490b, opening 494, passage 492, opening 496, and compartment 490c to the outlet 500. When the shaft 60 is moved, the openings 492 and 496 are moved from their respective positions in the compartments 490b and 490c, blocking communication between the inlet 498 and outlet 500. This, of course, defines typical valve operation.

The apparatus of FIG. 5 can also be used to direct fluid received, for example, at the left side of the apparatus (indicated by arrow 493) either to inlet 498 (which would become an outlet) or to outlet 500. This would be done by positioning shaft 60 with the opening 496 positioned in compartment 490b so that fluid would flow from compartment 490a through opening 494 and passage 492, out opening 496 into compartment 490b, and out the "outlet" 498. To direct fluid out the outlet 500, the passage 492 would be long enough to allow positioning opening 496 in compartment 490c while opening 494 is still positioned in compartment 490a. Then, with opening 496 positioned in compartment 490c, fluid would flow through opening 494 and passage 492, out the opening 496 into compartment 490c, and then out the outlet 500.

FIG. 5 shows a fragmented, side, cross-sectional view of a sphincter seal, including a shaft 60 disposed in an aperture 24 formed in a sheet of flexible material 20. In this embodiment, a lip 602 of the aperture 24 of the sheet of material 20 is formed to turn inwardly toward the interior of the valve housing (not shown) to effectively lie snugly about a portion of the shaft 60. A coil spring 606 is disposed about the lip 602 to urge the lip tightly against the shaft 60 to further enhance the seal between the sheet of material 20 and the shaft 60.

FIG. 6 shows a fragmented, side, cross-sectional view of a duplex sphincter shield arrangement, including a shaft 60, a first flexible sheet of material 620 having an aperture 624 formed therein, and a second sheet of flexible material 628 having an aperture 632 formed therein. A lip 636 of the aperture 624 of the sheet of material 620 is turned inwardly as shown, as is a lip 640 of the aperture 632 of the sheet of material 628, so that the lips are facing inwardly towards one another. A ring 644 is disposed between the sheets of material 620 and 628 to define a substantially airtight cavity 648 between the sheets of material 620 and 628, the ring 644, and the shaft 60.

With the configuration of FIG. 6, when the shaft 60 is moved longitudinally in either direction, the sheets of material 620 and 628 are flexed to increase the pressure in the cavity 648 and force the lip 636 and 640 in tighter contact with the shaft 60.

FIG. 7 is a fragmented, side, cross-sectional view of a duplex sphincter seal arrangement again including a shaft 60, a pair of flexible sheets of material 650 and 654, each with apertures 658 and 662 respectively, for receiving the shaft 60. However, instead of lips 664 of the sheet of material 650, and 668 of the sheet of material 654, turning inwardly towards one another as in FIG. 6, the lips are turned outwardly away from one another as shown. A ring 672 is disposed between the sheets of material 650 and 654 to define a cavity 676 similar to the cavity 648 of FIG. 6.

In operation, when the shaft 60 of the seal arrangement of FIG. 7 is reciprocated in either direction, a vacuum is produced in the cavity 676 so that outside pressure acts to force the lips 664 and 668 in tighter contact with the shaft 60, as desired.

The embodiments of the invention described herein are only examples of how the invention may be applied to specific devices. Modifications and variations of, for example, materials used, sizes and shapes of components, and equivalent structures will be apparent to those skilled in the art while remaining within the scope of the invention.

What is claimed is:

1. A valve comprising:
   a generally elongate housing with interior walls defining an interior cavity therein;
   a sheet of resilient material, with an aperture formed therein, disposed in the cavity and dividing it into first and second compartments, having a perimeter attached to the interior walls of the cavity, extending inwardly therefrom and being unsupported except where the perimeter is attached to the interior walls to enable volume of the first and the second compartments to vary in response to pressure changes within said first and second compartments;
   an inlet leading through the housing into the first compartment;

an outlet leading through the housing into the second compartment;

an elongate shaft disposed within and aligned with the cavity and extending through the aperture in the sheet, said shaft being adapted for reciprocating movement within the cavity; and an elongate interior passage extending lengthwise through the shaft, and including first and second openings which enable communication between the passage and the cavity, the openings being spaced from each other such that when the shaft is positioned so that the first opening is located in the first compartment, the second opening is located in the second compartment, to thereby provide fluid communication between the first and the second compartments.

2. The valve of claim 1 wherein at least two resilient sheets are disposed in the cavity and positioned so as to divide the cavity into at least three compartments.

3. The valve of claim 1 wherein the elongate shaft is positioned so that the first and second openings in the passage are located in the first or the second compartment, thereby cutting off fluid communication therebetween.

* * * * *